US00RE39047E

(19) United States
(12) Reissued Patent
Aizawa et al.

(10) Patent Number: US RE39,047 E
(45) Date of Reissued Patent: Mar. 28, 2006

(54) LUMINESCENCE BY REACTING AN ACRIDINIUM ESTER WITH SUPEROXIDE

(75) Inventors: Masuo Aizawa, Tokyo (JP); Yoshihito Ikariyama, deceased, late of Tokyo (JP); by Michiko Ikariyama, legal representative, Tokyo (JP); Eiry Kobatake, Tokyo (JP); Minoru Ogasawara, Tokyo (JP); Mitsunao Tanaka, Tokyo (JP)

(73) Assignee: Mitsubishi Kagaku Iatron, Inc., Tokyo (JP)

(21) Appl. No.: 09/800,670

(22) Filed: Mar. 8, 2001

(Under 37 CFR 1.47)

Related U.S. Patent Documents

Reissue of:
(64) Patent No.: 5,879,888
Issued: Mar. 9, 1999
Appl. No.: 08/741,120
Filed: Oct. 30, 1996

U.S. Applications:
(63) Continuation of application No. 08/232,256, filed as application No. PCT/JP93/01270 on Sep. 9, 1993, now abandoned.

(30) Foreign Application Priority Data

Sep. 9, 1992 (JP) ..... 4-266713

(51) Int. Cl.
*C12Q 1/68* (2006.01)
*G01N 33/533* (2006.01)

(52) U.S. Cl. ..... 435/6; 435/7.1; 435/25; 435/968; 422/82.07; 422/82.08; 436/800; 436/544; 436/546; 546/102; 546/104; 546/107; 546/530; 546/391.5

(58) Field of Classification Search ..... 435/6, 435/7.1, 25, 968; 436/544, 546, 800; 530/391.5; 422/82.07, 82.08; 546/102, 104, 107
See application file for complete search history.

(56) References Cited

U.S. PATENT DOCUMENTS 4,478,817 A * 10/1984 Campbell et al. ..... 436/547 X
4,927,769 A * 5/1990 Chang et al. ..... 436/518
4,933,276 A * 6/1990 Baret ..... 435/7.9
4,946,958 A * 8/1990 Campbell et al. ..... 546/104
5,306,624 A * 4/1994 Roelant ..... 435/39

FOREIGN PATENT DOCUMENTS

CA 2128530 A1 8/1993
EP 0256932 * 2/1988
EP 0361817 A2 4/1990
WO 9301308 * 1/1993

OTHER PUBLICATIONS

H. Ischiropoulos et al, "Effect of Interferon Inducers on Superoxide Anion Generation from Rat Liver Microsomes Detected by Lucigenin Chemiluminescence," Biochem.Biophys. Res. Comm. 161(3):1042–48 (1989).*

Kricka, "Chemiluminescent and Bioluminescent Techniques," Clin. Chem. 37(9):1472–81 (1991).*

J. Littig, "Quantitation of Acridinium Esters Using Electrogenerated Chemiluminescence and Flow Injection," Anal. Chem. 64(10):1140–44 (May 15, 1992).*

T. Peters et al, "Lucigenin Chemiluminescence as a Probe for Measuring Reactive Oxygen Species Production in *E. coli*," Anal. Biochem 186:316–19 (1990).*

M. Tosi et al, "A Rapid, Specific Assay for Superoxide Release from Phagocytes in Small Volumes of Whole Blood," Am. J. Clin. Path., 97(4):566–575 (Apr. 1992).*

A. White et al, Principles of Biochemistry, 4$^{th}$ edition (McGraw–Hill Book Company New York 1968) p. 220.*

* cited by examiner

*Primary Examiner*—Mary E. Ceperley
(74) *Attorney, Agent, or Firm*—Sughrue Mion, PLLC

(57) ABSTRACT

A light emitting method of an acridinium ester, comprising reacting said acridinium ester and a superoxide anion, and a method of detecting a substance to be examined, comprising detecting a light emitted by reacting a superoxide anion with an acridinium ester used as a label am described. It is possible to carry out the reaction not under strongly alkaline conditions but around the neutral point and to generate strong luminescence which is stable over a long period of time.

7 Claims, 4 Drawing Sheets

LUMINESCENCE BY REACTING AN ACRIDINIUM ESTER WITH SUPEROXIDE

Matter enclosed in heavy brackets [ ] appears in the original patent but forms no part of this reissue specification; matter printed in italics indicates the additions made by reissue.

This is a Continuation of application Ser. No. 08/232,256, filed as PCT/JP93/01270, Sep. 8, 1993 published as WO94/05742, Mar. 17, 1994, now abandoned.

TECHNICAL FIELD

The present invention relates to a light emitting method of an acridinium derivative by reacting a superoxide action ($O_2$) with the acridinium derivative and to a method of detecting a substance to be examined, utilizing a light emitted from the acridinium derivative as a label.

BACKGROUND ART

Along with the progress in diagnostic or medical technology, various methods of detection of particular substances contained in very minute quantities in serum and other biological specimens have been developed and put into use for enabling the early discovery of various diseases and for confirming the effects of therapy. The particular substances to be examined are, for example, various types of proteins, nucleic adds, drugs, and other biological substances. For the purpose of quantitative or qualitative examination of the same, a label as a signal generating source is attached in advance to substances having affinity with such particular substation to be examined, for example, antibodies and antigens where the substance to be examined is a protein; complementary nucleic acids whom the substance to be examined is a nucleic acid; and an antibody where the substance to be examined is a chug. The labeled substance having affinity with the substance to be examined and the sample containing the substance to be examined are brought into contact with each other to produce a conjugate of the substance to be examined and the labeled substance having affinity therewith. Then, the conjugate is separated by various methods, the signal generating source of the label is activated, and the signal is detected by various meant. As a result, the amount or the existence of the substance to be examined can be determined.

Numerous substances have been developed and supplied for practical we as such a labeling substance, for example, radioactive substances, fluorescent substances, enzymes, or metal colloids. In recent years, however, the chemiluminescence method using an acridinium derivative has drawn attention in view of its high sensitivity. Strong luminescence of the acridinium derivative can be generated by reaction with hydrogen peroxide ($H_2O_2$) under strong alkaline conditions (EP-A 830629 etc.)

An attempt has also been made to electrochemically emit light from the acridinium derivative (Anal. Chem. 64,1140, 1992). According to this repeat acridinium derivatives are electrochemically inert, but when a potential of −1.0V (vs. Ag/AgCl) is applied to the electrode under alkaline conditions (pH=12), the dissolved oxygen is reduced to produce hydrogen peroxide. The resulting hydrogen peroxide is reacted with acridinium derivative to generate luminescence. The means for electrochemically emitting light from a chemiluminescent substance is one of the key techniques for realization of immunosensors. More particularly, these is a possibility to be able to simply generate luminescence only by applying a potential to an electrode incorporated in the season as a means for generating luminescence of a chemiluminescent substance. The above technique is advantageous to small-sized devices such as sensors. To generate luminescence of an acridinium derivative, however, two steps are required as mentioned above; first rendering to the strongly alkaline conditions, then applying a potential to the electrode. In practice, problems remain to be solved in applying the above technique to an immunosensor.

In the meanwhile, there is a method of semiquantitatively detecting such a substance to be examined, namely so-called blotting, wherein a sample containing the substance to be examined is treated with electrophoresis or the like to separate the substances therein; the separated substances are transferred to and adsorbed on a nitrocellulose film or the like as they are; a labeled substance carrying a substance as a signal generating source and having affinity with the substance to be examined is banded with the substance to be examined which had been separated and adsorbed on the film, and then the signal generating source is activated to detect the substance to be examined. In this method, it is also possible to detect a substance with an extremely high precision, using chemiluminescence as the detecting means. In the past, however, an enzyme was used as the signal generating source in many cases, and luminol or an adamantane derivative (AMPPD) which can generate luminescence by an enzymatic reaction was used as the luminescent substance. That is, light is emitted from the luminescent substance by carrying out can enzymatic reaction of the signal generating source, and a photosensitive film is exposed with the emitted light to detect the signal.

A luminescent substance was not directly used as a signal generating source in blotting in the past, because the luminescence ends in several seconds when the luminescent substance is used as the signal generating source, and thus an amount of light sufficient to expose a photosensitive film cannot be obtained. Therefore, highly sensitive detection was performed by means of a method wherein an enzyme was used as the signal generating source, and an excess amount of a luminescent substance capable to generate luminescence by, the enzymatic reaction therewith was charged so as to emit light for a somewhat long period of time and expose the photosensitive film. Nevertheless, no suitable enzyme capable of generating luminescence by an enzymatic reaction was known for acridinium derivatives in the past. Thus, acridinium derivatives were not used in this field, although having a higher yield of luminescence in comparison with luminol or the like.

The reason why a suitable enzyme was not known is the mechanism of luminescence of the acridinium derivatives. For example, it is known that can acridinium derivative generates luminescence by the reaction with hydrogen peroxide, act it may be considered that luminescence can be generated using an enzymatic reaction, that ice, a reaction between $H_2O_2$ produced by an enzymatic reaction of oxidase such as glucose oxidase and an acridinium derivative. Unless the acridinium derivative is under strong alkaline conditions, however, the acridinium derivative does not strongly emit light. No enzymes an known which retain their sufficient activity and produce hydrogen peroxide under such strong alkaline conditions.

Further, it is known that an acridinium derivative generates less luminescence under strong alkaline conditions. Accordingly, even if there existed a suitable enzyme which could retain sufficient activity under strong alkaline conditions, there was still the problem that it would not be possible to make sufficient use of the luminescent ability inherently possessed by ad acridinium derivative, under luminescent conditions of strongly alkaline conditions for a long term.

As explained above, there was the problem that an acridinium derivative had to be used under strongly alkaline conditions in the conventional light-emitting techniques, so luminescence could not strongly be generated. Therefore, there were considerable limits to its application, despite the high yield of luminescence.

The present inventors engaged in intensive research on improvements of the light emitting method of acridinium derivatives to broaden the application fields thereof, whereupon the invention surprisingly discovered that strong luminescence is generated even around the neutral condition by reacting an acridinium derivative with the one-electron reluctant of dissolved oxygen, a superoxide anion ($O_2$'). The mechanism of the above luminescence is based on a principle completely different from that of the conventional chemiluminescent method wherein hydrogen peroxide is used under strongly alkaline conditions. Further, because luminescence is generated around neutral condition, the various problems in the prior art can be solved all at once.

DISCLOSURE OF INVENTION

Accordingly, the present invention relates to a light emitting method of an acridinium derivative, characterized by reacting said acridinium derivative and a superoxide anion.

Further, the present invention relates to a method of detecting a substance to be examined, characterized by detecting a light emitted by reacting a superoxide anion with an acridinium derivative as a label.

BEST MODE FOR CARRYING OUT THE INVENTION

Figure 1:
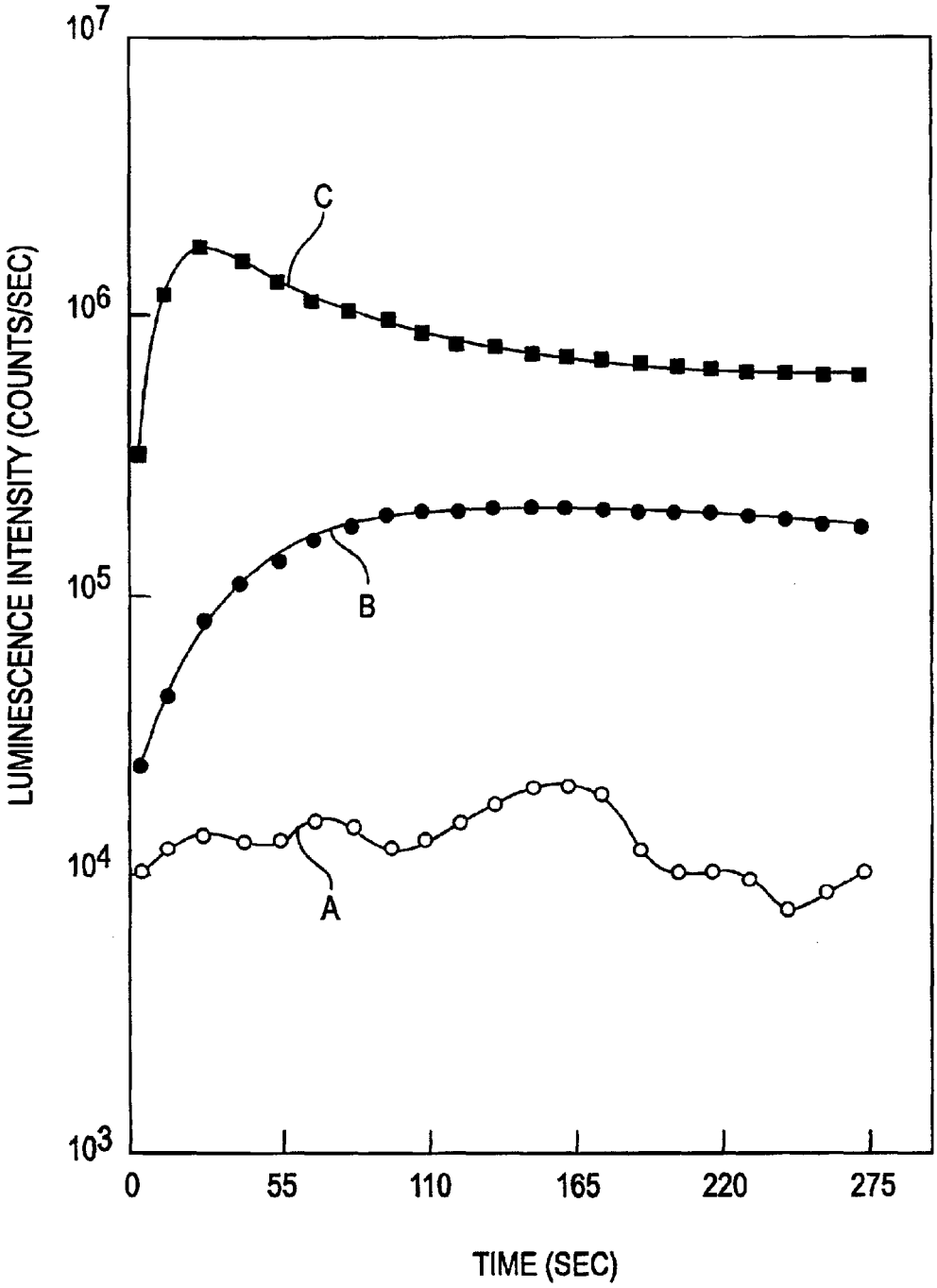
FIG. 1 is a graph showing the results of electrochemically generating luminescence of an acridinium derivative in the presence of a flavin compound.

The acridinium derivative which can be used in the present invention is a compound in which the ring nitrogen atom of the acridine ring is quarternized and has a counter ion and further has a substituent at the 9-position of the acridine ring via a —C(=0)— group, and optionally has one or more substituents at 1 to 8 positions, that is, a compound of the general formula (1):

(1)

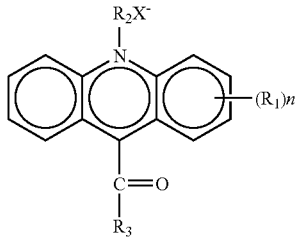

wherein a is 0 or an integer of 1 to 8, $R_1$, $R_2$, and $R_3$ are, independently, substituents, and X- is a counter ion. The acridinium derivative of the general formula (1) is known as a chemiluminescent substance, as described for example in EP-A 082636, Japanese Unexamined Patent Publications (Kokai) No. 63-57572, No. 63-101368 and No. 63-112564, and Japanese National Publication Kohyo) No. 3-505373. A preferred acridinium ester has the following structure

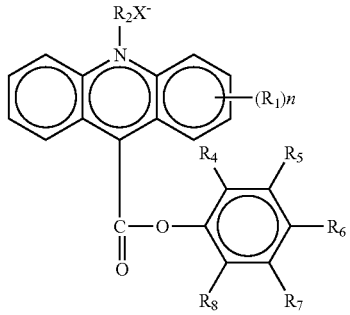

These acridinium derivatives may be used in the method of the present invention. More specifically, $R_1$ can be selected from the group consisting of a hydrogen, amino, carboxyl, hydroxyl, alkoxyl, nitro and halide group; $R_2$ can be selected from the group consisting of a hydrogen, alkyl, alkenyl, alkenyl and aryl group; $R_3$ can be a substituted phenoxy moiety; $R_4$ and $R_6$ each can be an alkyl, alkenyl, alkynyl, aryl, alkoxyl, amino, amino, sulfonamide or sulfide group; $R_5$ and $R_7$ each can be a hydrogen, amino, carboxyl, hydroxyl, alkoxyl, nitro or halide group; $R_6$ can be a hydrogen, amino, carboxyl, hydroxyl, alkoxyl, nitro or halide group or $R_6$ can be of the formula:

$$—R_9—R_{20}$$

wherein $R_9$ is not required, but when present can be an alkyl, aryl or akenyl group; and $R_{10}$ can be

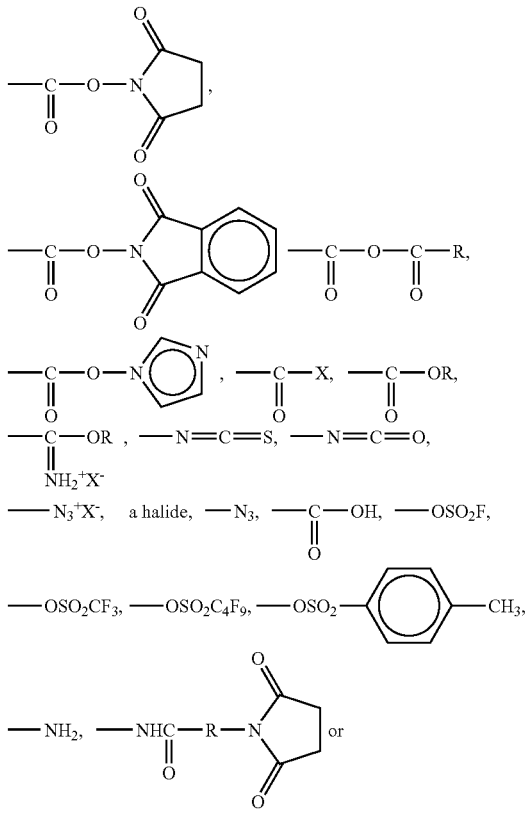

-continued

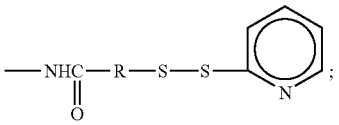

wherein X can be $CH_3SO_4$—, $OSO_2F$—, a halide, $OSO_2CF_3$—, $OSO_2C_4F_9$— or

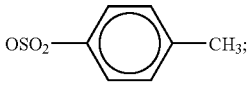

and R can be an alkyl, aryl or aralkyl group, and $R_5$, $R_6$ and $R_7$ of the phenoxy ring are interchangeable. A particularly preferred compound is 4-[2-(succinimyzyloxycarbonyl) ethyl]phenyl-10-methylacridinium-9-carboxylate fluorosulfate (SPMA) Kokai No. 63-101368 provides, in part, a luminescent compound comprising a polysubstituted aryl acridinium ester selected from the group having the following structure:

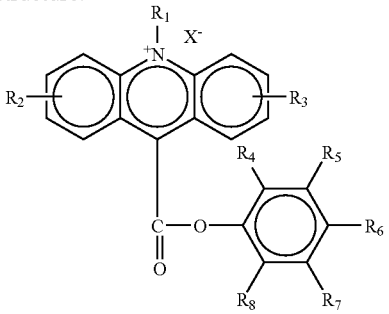

wherein R, is an alkyl, alkenyl, alkenyl, or aryl group; $R_2$, $R_3$, $R_5$, or $R_7$ are a hydrogen amino, carboxyl, hydroxyl. alkoxyl, nitro, or halide group; $R_4$ or $R_5$ are an alkyl, alkenyl, alkenyl, aryl, alkoxyl, amino, amino, sulfonamido, or sulfide group; $R_6$ represents the following substituent:

$R_6$—$R_9$—$R_{10}$ wherein $R_9$ is not required but optionally can be an alkyl, aryl, or aralkyl group, and $R_{10}$ is selected from the following:

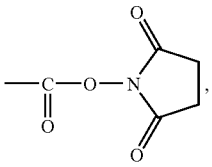

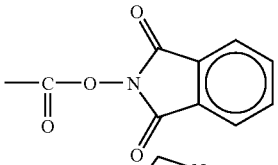

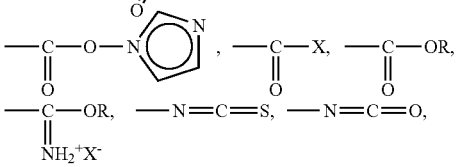

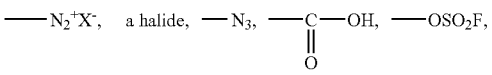

-continued

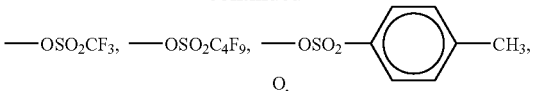

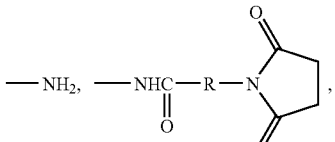

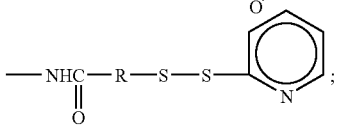

X is $CH_3$-$SO_4$—, $OSO_2P$—, a halide, $OSO_2CF_3$—, $OSO_2C_4F_9$—, or

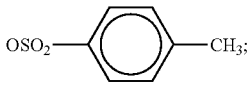

R is alkyl, aryl, or aralkyl group; and $R_5$, $R_6$ and $R_7$ substituent positions no the phenoxy ring are interchangeable.

EP-A 082 636 provides, in part, a compound represented by the general formula (1)

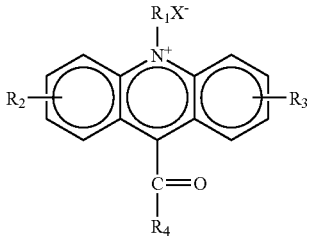

in which $R_1$ represents H, $C_1$–$C_{10}$ optionally substituted alkyl, alkenyl, alkenyl or aryl, $R_2$, $R_3$ are preferably, hydrogen, amino, substituted amino, carboxyl, hydroxyl, alkoxyl, nitro-, or halide substituents, and $R_4$ is preferably an optionally substituted phenoxy-moiety. According to a preferred feature of the invention an ester linkage exists between the acridinium and phenyl moieties as exemplified in the following formula:

(2)

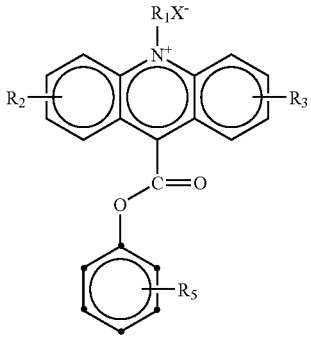

where $R_1$ comprises one of the following:

(a)

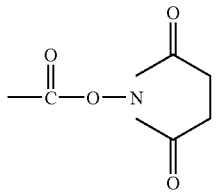

(b)

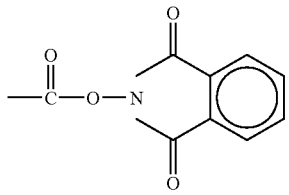

(c) —NCS (d)

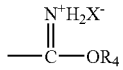

(e) -halide (f) -azide where $R_6$ represents groups such as $R_1$ and X represents a halide. Preferably $R_5$ is Linked to the phenyl residue via carbon, nitrogen or oxygen containing groups which are optionally substituted by substituents of a hydrophilic nature.

In the light emitting, method of the present invention, a superoxide anion, ($O_2$) is reacted with the acridinium derivative. The superoxide anion used in the method of the present invention can be ;produced by any method. For example, when oxygen dissolved in an electrolytic solution (that is dissolved oxygen) is electrochemically reduced, it is considered that stable hydrogen peroxide is produced through superoxide anions, hydroperoxy radials, and hydroperoxide ions due to successive ECEC reactions (E: electrochemical, C: chemical) (Chemistry of Active Oxygen Species, Gakkaj Shuppan Center).

Therefore, if an acridinium derivative exists as a reaction species for a superoxide anion at the time when a superoxide anion is produced by one-electron reduction, it is considered that the acridinium derivatives should generate luminescence. However, in fact, them is generated a little luminescence around the neutral region in the range of the electrode potential whom no hydrogen gas is produced (0 to about −0.7V vs. Ag/AgCl). The reason is believed to be the low production rate of the superoxide anion.

On the other hand, the prevent investors discovered that it is possible to strongly generate luminescence of an acridinium derivative even around the neutral region by electrochemically reducing dissolved oxygen in the presence of a flavin compound to emit light from the acridinium derivative. Further, the present inventors confirmed that a flavin compound catalyzes the production of a superoxide anion.

Examples of the flavin compound which can be used as flavin adenine dinucleotide (FAD), flavin mononucleotide, and riboflavin.

Therefore, when a superoxide anion is electrochemically produced, it is preferable to use a catalyst such as the above flavin compounds. More particularly, when FAD is used as the catalyst, it is preferable to adjust the concentration of. FAD to about $1\times10^{-9}$M to $11\times10^{-4}$M in a 50 mM (or more) conventional or a conventional buffer containing 0.15M NaCl, apply potential of −0.3 to −0.7V (vs. Ag/AgCl) and adjust a pH of the buffer to 6 to 10.

Further, it is possible to use an enzyme such as xanthine oxidase to produce a superoxide anion in the light emitting method according to the present invention. Xanthine oxidase produces a superoxide anion, ($O_2^-$) by a reaction with substrates, namely, hypoxanthine and xanthine. Accordingly, it is possible to generate luminescence of an acridinium derivative by the superoxide anion produced in the reaction with the enzyme.

For example, it is possible to emit light from an acridinium derivative by producing a superoxide anion at a pH enabling xanthine oxidase active, for example, a pH of 5 to 11, preferably 6 to 10, in a conventionally known buffer solution capable of buffering the above pH range, using xanthine oxidase and xanthine or hypoxanthine as a substrate. The concentrations of the reactants ate suitably adjusted.

It is possible to perform immunoassay wherein an acridinium derivative is used as a label, using the light emitting method of an acridinium derivative. Whereas the mechanism of using action of $H_2O_2$ under strongly alkaline conditions is used in the conventionally known chemiluminescence method of an acridinium derivative, a superoxide anion is made to act in the present invention. Therefore, the present invention does not requite strongly alkaline conditions and thus may be applied to a wide range of immunoassay methods.

The method of immunoassay according to the present invention is characterized by use of an acridinium derivative as a label and use of chemiluminescence generated by the action of a superoxide anion on the label as a signal. The features in the conventional immunoassay other than those mentioned as above can be used as they are.

Therefore, there may be mentioned, as a sample, body fluids, such as blood, serum, plasma, urine, saliva or spinal fluid, cell or tissue extracts a the like, and as a substance to be examined, biologically active substances contained in the biological components in the above samples and capable of being detected by an immune reaction, as in the conventional method of immunoassay. More particularly, examples of the substance to be examined are proteins, enzymes, polysaccharides, lipids, or nucleic acids, for example, various antigens, antibodies, receptors, or the like. More specifically, them may be mentioned fibrinogen, albumin, C-reactive proteins, anti-streptolysin O, rheumatoid factors, α-fetoprotein (AFF), Treponema palladium antibodies, anti-HBs antibodies, anti-HBc antibodies, anti-HBe antibodies, anti-HTLV antibodies, anti-HIV antibodies, or the like. Further, it is also possible to detect low molecular weight compounds, haptenes, such as hormones, or various drugs such as antiepileptic agent, or antibodies against haptenes.

The acridinium derivative maybe bonded to the substance to be labeled, wing various methods in accordance with the types of the acridinium derivatives. For example, when the acridinium derivative is SPMA, the substance to be labeled and the SPMA may be mixed and purified under alkaline conditions. Further, in the can of an acridinium derivative having an amine group, it is possible to use the maleimide cross-linking method or the like to bond it to the substance to be labeled.

When detecting for example, an antigen in a serum sample by the immunoassay method according to the present invention, an immune reaction can be carried out between an antibody (for example, a monoclonal antibody) labeled with the acridinium derivative by the above-mentioned method and specifically recognizing said antigen and the antigen in the sample and if necessary, the unbound labeled antibody is removed by B/F separation. Then, a superoxide anion is electrochemically produced in the presence of a flavin compound, and the luminescence of the acridinium derivative is measured to dated the antigen.

Further, when detecting, for example, an antigen in a serum sample by the immunoassay method according to the present invention wherein an enzymatic reaction is used, an immune reaction can be carried out in the same manner as above, and a superoxide anion is produced using, for example, xanthine oxidase turn xanthine or hypoxanthine in the reaction system. Then, the luminescence of the acridinium derivative is measured to detect the antigen.

In addition to the above immunoassay method, an acridinium derivative may be used according to the present invention in the detection, for example, blotting, of a nucleic acid by making use of the affinity between the nucleic acid and its complementary nucleic acid, in the same manner as the above immunoassay method.

EXAMPLE

The present invention now will be further illustrated by, but is by no means limited to, the following examples.

Example 1

As an acridinium derivative, 4-[2-(succinimyzyloxycarbonyl)ethyl]phenyl-10-methylacridinium-9-carboxylate fluorosulfate (SPMA) was used. A platinum electrode (9 mm×9 mm×0.5 mm) as a wolfing electrode, a platinum coil electrode (diameter=0.5 mm) as a counter electrode, and an Ag/AgCl electrode to a reference electrode were aced. A luminescence all used was a spectrophotometer grass cuvette (1 cm) which can be affixed to a light-receiving surface of a photomultiplier tube. A sample solution was prepared by adjusting a concentration of SPMA to $1.67\times10^{-7}$ with a phosphate buffer (pH 8.0) containing 0.15M sodium chloride. As the flavin compound, flavin adenine dinucleotide (FAD) was used. Two cases were examined: the case wherein the FAD was contained in the sample solution in a concentration of $6.67\times10^{-6}$M and the case wherein an FAD adsorbing electrode prepared by adsorbing FAD to a working electrode (platinum electrode) was used. FAD was adsorbed on the working electrode by immersing the electrode in a 2 mM-FAD solution and carrying out 10 cycles of cyclic voltammetry in the range of −0.5V to 0.2V (vs. Ag/AgCl) at a scan speed of 50 mV/sec.

The sample solution was charged into the luminescence cell, the electrodes were connected to the luminescence cell, and then a potential of −05V (vs. Ag/AgCl) was applied to the working electrode and at the same time the amount of luminescence was measured by a photon counter. The results are shown in FIG. 1.

As shown in FIG. 1, in comparison with the control experiment (curve A in FIG. 1) where no FAD was present, about 10 times the amount of luminescence was shown in the FAD-containing sample; solution (curve B in FIG. 1), and, about 100 times the luminescence was exhibited in the FAD adsorbing electrode (curve C in FIG. 1).

Example 2

Figure 2:
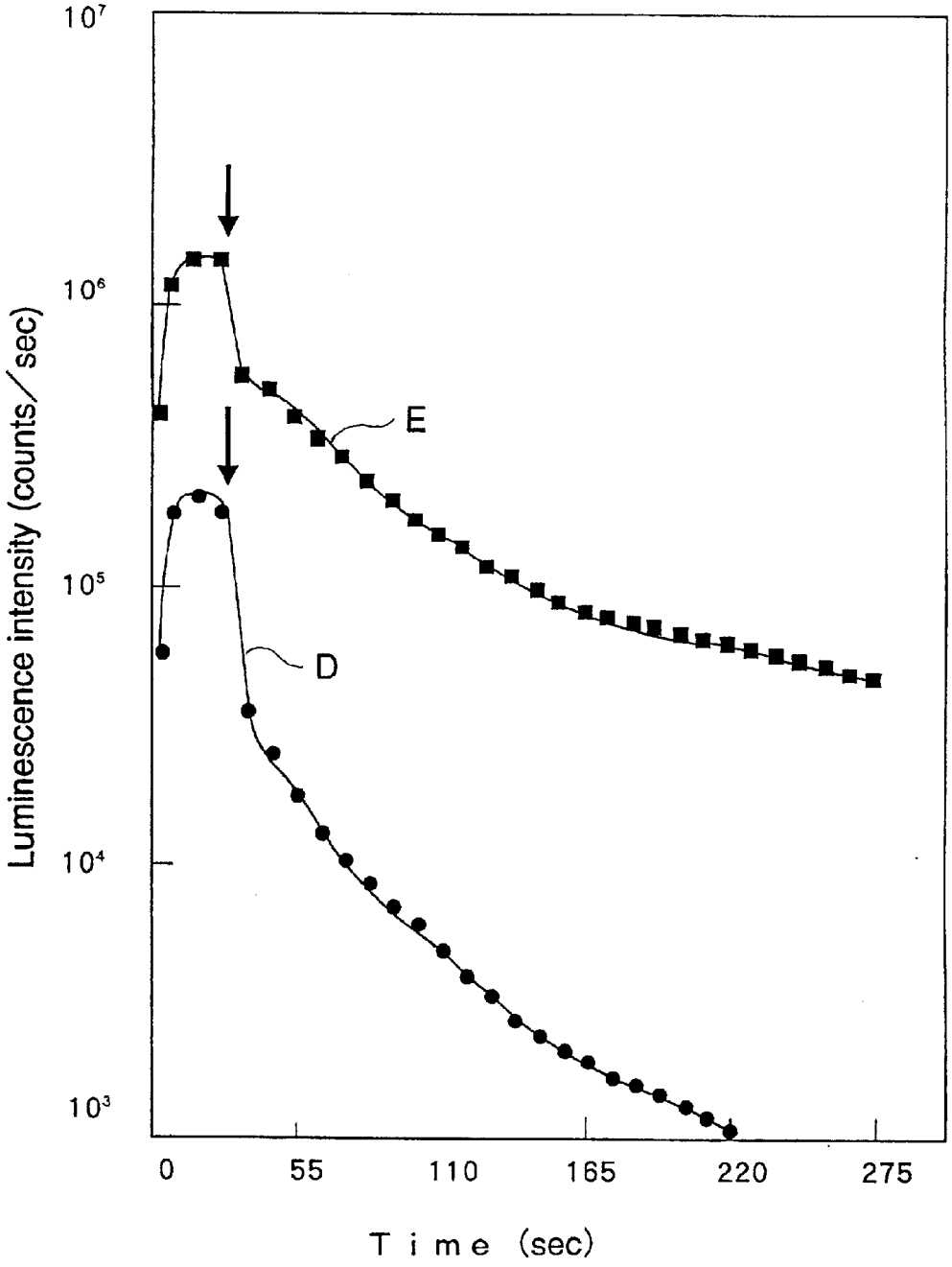
FIG. 2 is a graph showing the action of the superoxide anion in the electrochemical luminescence of the acridinium derivative.

The procedure described in Example 1 was repeated, except that 714 units of superoxide dismutase (SOD: Sigma) were added to the luminescence cell after 27.5 seconds hum the beginning of the luminescent reaction, and then the amount of luminescence was similarly measured. The results are shown in FIG. 2. In FIG. 2, the curve D shows the case of a sample solution containing FAD, the curve E shows the case of an FAD absorbing electrode, and the downward arrows show the time when the superoxide dismutase was added.

As shown in FIG. 2, it was confirmed that when SOD is added, the amount of luminescence is remarkably reduced. SOD is an enzyme which catalyzes the reaction of $$2O_2^- + 2H^+ \rightarrow H_2O_2 + O_2$$

The amount of luminescence is reduced at the same time as SOD is added because the superoxide anion is converted to $H_2O_2$ and disappears. Accordingly, it is considered that a luminescence of the acridinium derivative under the above conditions (pH 8.0) is generated by a reaction with a superoxide anion. Further, it is suggested that the luminescence in each of the FAD-containing sample solution (curve B) and the FAD adsorbing electrode (curve C) is stronger than that of the control (curve A) in FIG. 1, bemuse the amount of the superoxide anion produced is larger in the presence of FAD than in its absence, and that FAD catalyzes the production of a superoxide anion.

The above procedure was repeated, except that FMN (flavin mononucleotide) was used instead of FAD. The results similar to the above were obtained.

As mentioned above, it was possible to generate an extremely strong and stable luminescence for a long term even around neutral conditions, by producing a superoxide anion and reading the superoxide anion with an acridinium derivative in the presence of a flavin.

Example 3: Electrochemical Measurement

In this example, a protein (rabbit IgG: Miles-Yeda) was chemically modified with an acridinium derivative (SPMA) and a standard curve of the protein was produced by electrochemical luminescence. 100 μl of 0.5 mM SPMA dimethylformamide solution and 500 μl of 160 μg/ml rabbit IgG 0.1M phosphate: buffer (pH 8.0) were pouted into a test tube and reacted at room temperature for 15 minutes. Then, 1 ml of 10 mg/ml lysin hydrochloride was added, the mixture was allowed to stand for 15 minutes. Thereafter, the mixture was poured into G25 column (14×100 mm) to obtain a conjugate of IgG and the acridinium derivative.

Figure 3:
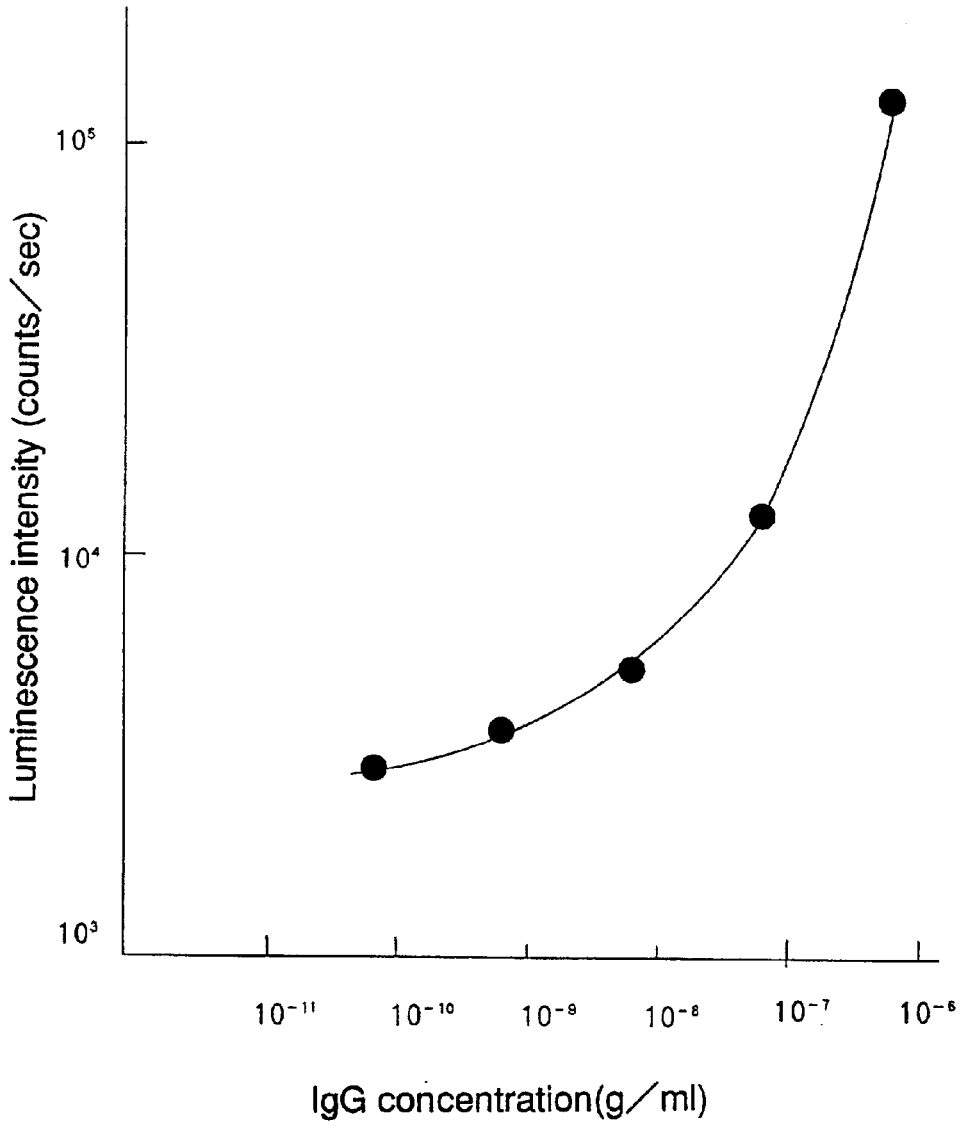
FIG. 3 shows a standard curve of IgG labeled with an acridinium derivative for detection by electrochemical luminescence.

The measurement was performed, using electrodes and luminescence cell used in Example 1. As the working electrode, an electrode prepared by adsorbing FAD by the method described in Example 1 was used. Further, a ample solution was prepared using a phosphate buffer (pH 8.0) containing 0.15M sodium chloride. The potential applied was −0.5V (vs. Ag/AgCl) and the amount of luminescence was measured after 27.5 seconds from the application of the potential, the results are shown in FIG. 3. In this example, it was possible to measure $7\times10^{-9}$ g/ml of IgG.

Example 4: Measurement by Enzyme

Figure 4:
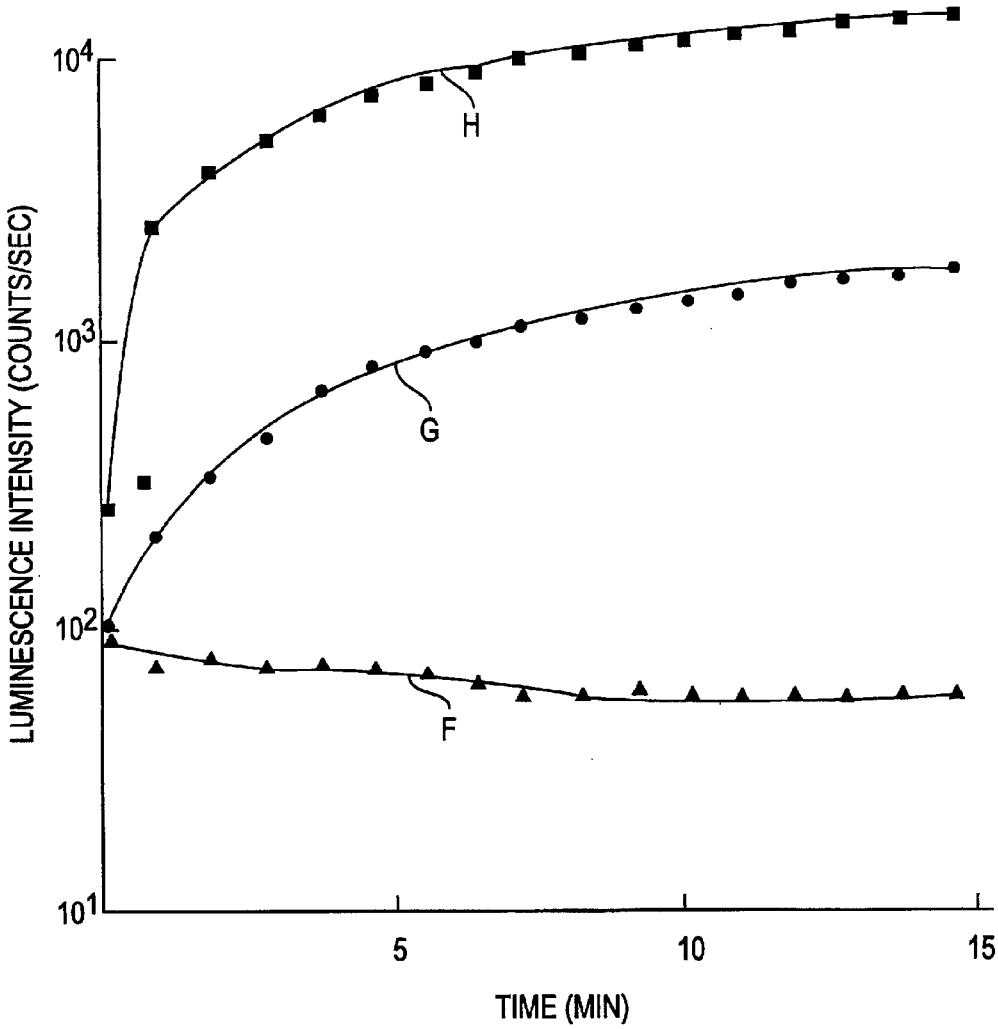
FIG. 4 is a graph showing, the results of luminescence of an acridinium derivative with an enzyme.

In this example, the measurement was carried out for the superoxide anion produced by an enzyme. Xanthine oxidase (from cow's milk: Boehringer Mannheim) solution was prepared with a phosphate buffer (pH 7.4) containing 0.15M sodium chloride. 1 ml of the resulting enzyme solution was poured into a luminescence cell. Then, 200 l of a luminescence initiator (12.5 μM SPMA aqueous solution containing 0.5 mM xanthine) was added to the luminescence cell and the change In the amount of luminescence with time was measured. The results am shown in FIG. 4. In FIG. 4, the curve F is a control sample not containing xanthine oxidase, the curve G is a sample containing 33 pmol of xanthine oxidase, and the curve H is a sample containing 33 pmol of xanthine oxidase. As shown in FIG. 4, it was possible to generate stable luminescence with growth type characteristics for a long term.

INDUSTRIAL APPLICABILITY

According to the light emitting method of the present invention, luminescence is generated by an action of a superoxide anion to an acridinium derivative, so it is not necessary to use strongly alkaline conditions as in the conventional methods. The reaction can be carried out around the neutral point to generate strong luminescence which is stable over a long period of time. Further, when an acridinium derivative is used as a label and a superoxide anion is made to act on the label around the neutral point, it is possible to obtain a strong luminescence which is stable over a long period of time. Thus it is possible to provide a method of immunoassay which is accurate and has a high precision.

We claim:

1. A method for emitting chemiluminescence from an acridinium ester in an immunoassay, a hybridization assay or an immunoblot assay, wherein said ester is a compound of the formula (2):

(2)

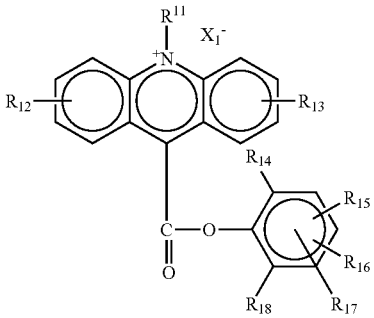

wherein $R_{11}$ is an alkyl, alkenyl, alkynyl or aryl group; $R_{12}$, $R_{13}$, $R_{15}$ and $R_{17}$ are independently a hydrogen atom, halide atom, amino, carboxyl, hydroxyl, alkoxyl or nitro group; $R_{14}$ and $R_{18}$ are independently an alkyl, alkenyl, alkynyl, aryl, alkoxyl, amino, amido, sulfonamido or sulfide group; $R_{16}$ is —$R_{19}$—$R_{10}$; $R_{19}$ is not required but optionally can be an alkyl, aryl or aralkyl group; $R_{10}$ is selected from the group consisting of:

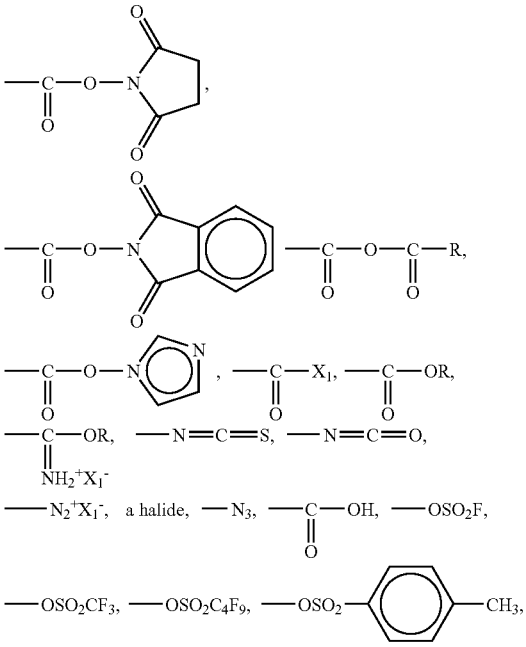

-continued

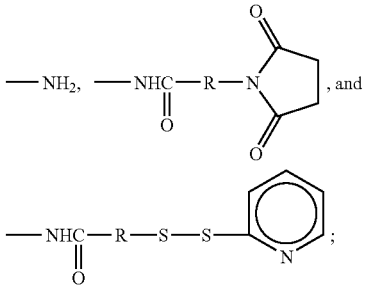

$X_1$ *is* $CH_3SO_4^-$, $OSO_2F^-$, a halide, $OSO_2CF_3^-$, $OSO_2C_4F_9^-$, or

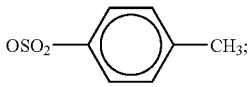

and R is an alkyl, aryl or aralkyl group; or said ester is a compound of the formula (3a):

(3a)

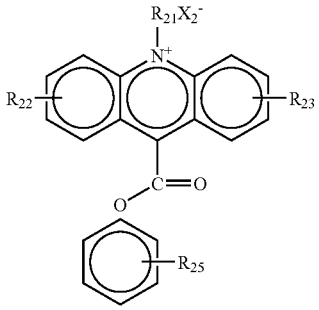

wherein $R_{25}$ comprises one of the following:

(a)

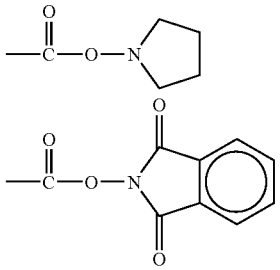

(c)

—NCS (d)

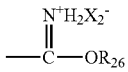

(e)

-halide or (f)

-azide;

$R_1$, and $R_{26}$ are independently a hydrogen atom or $C_1$–$C_{10}$ optionally substituted alkyl, alkenyl, alkynyl or aryl group; $R_{22}$ and $R_{23}$ are independently a hydrogen atom, halide atom, amino, substituted amino carboxyl, hydroxyl, alkoxyl or nitro group; and $X_2$ is a halide atom, comprising reacting at a pH of 6 to 10 said acridinium ester and a superoxide anion produced in situ by electrochemical reduction of oxygen dissolved in an electrolyte using electrodes in the presence of a flavin compound, wherein said acridinium ester is attached as a label to a reagent in said immunoassay, hybridization may or immunoblot assay.

2. The method of claim 1, wherein the electrochemical reduction is performed in the presence of $1\times10^{-9}$M to $1\times10^{-4}$M of the flavin compound at a potential of −0.3 to −0.7V (vs. Ag/AgCl).

3. The method of claim 1 wherein the electrochemical reduction comprises use of an electrode comprising said flavin compound.

[4. The method of claim 1, wherein the acridinium ester is 4-[2-succinimyzyloxycarbonyl)ethyl]phenyl-10-methylacridinium-9-carboxylate fluorosulfate.]

5. A method of detecting a substance to be examined in a sample in an immunoassay, hybridization assay or immunoblot assay, comprising, binding a chemiluminescent labeled substance having affinity for said substance to be examined with said substance to be examined in a sample to produce a complex of said substance to be examined and said chemiluminescent labelled substance having affinity therefor, separating said complex;

reacting said chemiluminescent label with a superoxide anion at a pH of 6 to 10, said label being an acridinium ester of the formula (2):

(2)

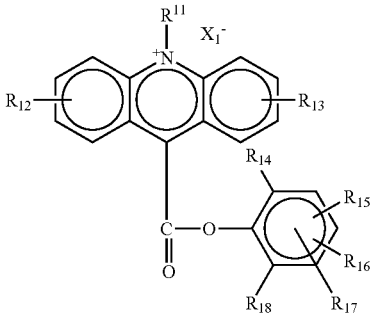

wherein $R_{11}$ is an alkyl, alkenyl, alkynyl or aryl group; $R_{12}$, $R_{13}$, $R_{15}$ and $R_{17}$ are independently a hydrogen atom, halide atom, amino, carboxyl, hydroxyl, alkoxyl or nitro group; $R_{14}$ and $R_{10}$ are independently an alkyl, alkenyl, alkynyl, aryl, alkoxyl, amino, amido, sulfonamido or sulfide group; $R_{14}$ is —$R_{19}$—$R_{10}$; $R_{19}$ is not required but optionally can be an alkyl, aryl or aralkyl group; $R_{10}$ is selected from the group consisting of:

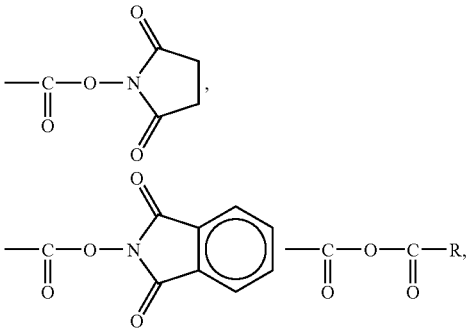

-continued

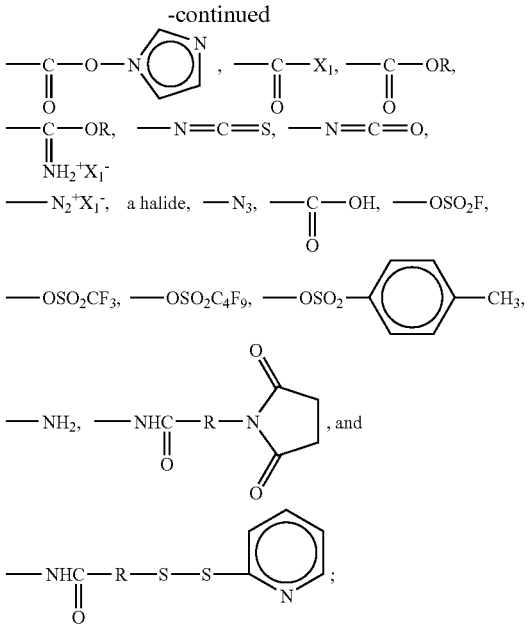

$X_1$ is $CH_3SO_4$—, $OSO_2F$—, a halide, $OSO_2CF_3$—, $OSO_2C_4F_9$—, or

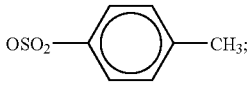

and R is an alkyl, aryl or aralkyl group; or said label is an acridinium ester of the formula (3a):

(3a)

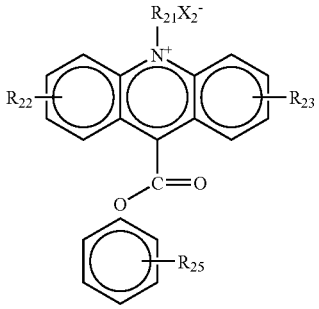

wherein $R_{25}$ comprises one of the following:

(a)

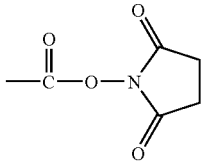

(b)

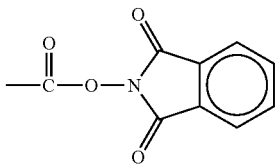

-continued (c)

$$-NCS$$

(d)

$$-\overset{\overset{N^+H_2X_2^-}{\|}}{C}-OR_{26}$$

-halide or (e)

-azide; (f)

$R_{21}$ and $R_{26}$ are independently a hydrogen atom or $C_1$–$C_{10}$ optionally substituted alkyl, alkenyl, alkynyl or aryl group; $R_{22}$ and $R_{23}$ are independently a hydrogen atom, halide atom, amino, substituted amino, carboxyl, hydroxyl, alkoxyl or nitro group; and X2 is a halide atom; wherein said superoxide anion is produced in situ by electrochemical reduction of oxygen dissolved in an electrolyte using electrodes in the presence of a flavin compound; and measuring luminescence of said chemiluminescent label to detect said substance to be examined.

6. The method of claim 5 wherein said binding step in said hybridization assay is reaction between a nucleic acid and a nucleic acid complementary thereto.

[7. The method of claim 5 wherein the acridinium ester is 4-[2-succinimyzyloxycarbonyl)ethyl]phenyl-10-methylacridinium-9-carboxylate fluorosulfate.]

*8. A method for emitting chemiluminescence from an acridinium ester in an immunoassay, a hybridization assay or an immunoblot assay, where said ester is 4-[2-(succinimidyloxycarbonyl)ethyl]phenyl-10-methylacridinium-9-carboxylate fluorosulfate, comprising reacting at a pH of 6 to 10 said acridinium ester and a superoxide anion produced in situ by electrochemical reduction of oxygen dissolved in an electrolyte using electrodes in the presence of a flavin compound wherein said acridinium ester is attached as a label to a reagent in said immunoassay, hybridization assay or immunoblot assay.*

*9. A method of detecting a substance to be examined in a sample in an immunoassay, hybridization assay or immunoblot assay, comprising, binding a chemiluminescent labeled substance having affinity for said substance to be examined with said substance to be examined in a sample to produce a complex of said substance to be examined and said chemiluminescent labelled substance having affinity therefor; separating said complex; reacting said chemiluminescent label with a superoxide anion at a pH of 6 to 10, said label being a 4-[2-(succinimidyloxycarbonyl)ethyl] phenyl-10-methylacridinium-9-carboxylate fluorosulfate; wherein said superoxide anion is produced in situ by electrochemical reduction of oxygen dissolved in an electrolyte using electrodes in the presence of a flavin compound; and measuring luminescence: of said chemiluminescent label to detect said substance to be examined.*

* * * * *

UNITED STATES PATENT AND TRADEMARK OFFICE

CERTIFICATE OF CORRECTION

PATENT NO. : RE 39,047 E
APPLICATION NO. : 09/800670
DATED : March 28, 2006
INVENTOR(S) : Masuo Aizawa et al.

It is certified that error appears in the above-identified patent and that said Letters Patent is hereby corrected as shown below:

On the title page item (63), U.S. Applications should read -- Continuation of application No. 08/232,256, filed as application No. PCT/JP93/01270 on September 8, 1993, now abandoned.--

Column 1, line 16, delete "$(O_2)$" and insert -- $(O_2^-)$--;

Column 3, line 10, delete "$(O_2')$" and insert -- $(O_2^-)$--;

Column 7, line 34, delete "$(O_2)$" and insert -- $(O_2^-)$--;

Column 12, line 14, delete "$X_{1\ is\ CH3}SO_4$-" and insert -- $X_1$ is $CH_3SO_4^-$ --;

Column 13, line 48, delete "$(R_{10})$" and insert -- $(R_{18})$ --; and

Column 14, line 26, delete "$X_1$ is $CH_3SO_4^-$, $OSO_2F^-$, a halide, $OSO_2CF_3^-$, $OSO_2C_4F_9^-$ or" and insert -- $X_1$ is $CH_3SO_4^-$, $OSO_2F^-$, a halide, $OSO_2CF_3^-$, $OSO_2C_4F_9^-$ or --.

Signed and Sealed this

Sixth Day of March, 2007

JON W. DUDAS
*Director of the United States Patent and Trademark Office*